(12) United States Patent
Codignola

(10) Patent No.: US 7,314,957 B2
(45) Date of Patent: Jan. 1, 2008

(54) AROMATIC GLYCOLS AND POLYOLS, PREPARATION PROCESS AND THEIR USE AS MONOMERS

(75) Inventor: Franco Codignola, Milan (IT)

(73) Assignee: Eurotecnica Contractors & Engineers S.p.A., Milan (IT)

( * ) Notice: Subject to any disclaimer, the term of this patent is extended or adjusted under 35 U.S.C. 154(b) by 235 days.

(21) Appl. No.: 10/510,409

(22) PCT Filed: Apr. 8, 2003

(86) PCT No.: PCT/EP03/03665

§ 371 (c)(1),
(2), (4) Date: Oct. 5, 2004

(87) PCT Pub. No.: WO03/085026

PCT Pub. Date: Oct. 16, 2003

(65) Prior Publication Data

US 2005/0215761 A1     Sep. 29, 2005

(30) Foreign Application Priority Data

Apr. 8, 2002  (IT) .......................... MI2002A0734

(51) Int. Cl.
 *C07C 233/65* (2006.01)
(52) U.S. Cl. ..................................... 564/156
(58) Field of Classification Search ................. 564/156
 See application file for complete search history.

(56) References Cited

U.S. PATENT DOCUMENTS

| 2,364,737 A |   | 12/1944 | McGrew |
| 3,929,731 A |   | 12/1975 | Volkova et al. |
| 3,935,162 A | * | 1/1976 | Golborn et al. ............. 524/124 |

FOREIGN PATENT DOCUMENTS

| DE | 10 02 326 |   | 2/1957 |
| DE | 38 24 961 | * | 1/1990 |
| EP | 0 191 582 | * | 6/1986 |

OTHER PUBLICATIONS

Branchaud et al, J. Org. Chem., vol. 52, 5475-5478, 1987.*
Chemical Abstracts, vol. 27, No. 18, Sep. 20, 1933 Columbus, OH, US "Discloses Resins for Aryl Sulfonamido Carboxylic Acidamides and the Products Obtained from Aryl Dicarboxylic-Acid-Amides:" p. 4698, George Walter, et al XP002230159.

* cited by examiner

*Primary Examiner*—Shailendra Kumar
(74) *Attorney, Agent, or Firm*—Hedman & Costigan PC; James V. Costigan

(57) ABSTRACT

Compounds are described, having the following general formula (A) $R(CONH-CHR_1OH)_m$ (A) and their use as monomers in polymerization and polycondensation reactions.

2 Claims, No Drawings

AROMATIC GLYCOLS AND POLYOLS, PREPARATION PROCESS AND THEIR USE AS MONOMERS

This application is a 371 of PCT/EP03/03665, filed Apr. 8, 2003.

The present invention relates to aromatic glycols and/or polyols, the relative use as monomers and the preparation process.

The state of the art normally describes the use of aliphatic glycols and/or polyols as co-monomers in the production of polyester resins, unsaturated polyester resins, thermoplastic polyester resins and polyurethane resins. It is known however that the introduction of aromatic rings in the chains of polyurethane resins or polyester resins enhances the chemical properties of these structures, such as an improved resistance to corrosion, oxidation with ultraviolet rays, temperatures, etc. and also allows the physico-mechanical characteristics to be enhanced. As of today, however, it has only been possible to insert these aromatic groups in the chains through the use of pure aromatic polycarboxylic acids in the case of polyester resins or with the use of aromatic isocyanates.

Further evidence of the importance and usefulness of inserting aromatic nucleuses in the chain of polyurethane or polyester resins, is obtained when, by substituting terephthalic acid, whose polycondensation leads to the production of PET (polyethyleneterephthalate) with 2,6-naphthalenedicarboxylic acid, i.e. by introducing two benzene rings into the chain instead of one single ring, a product, PEN (polyethylenenaphthalate) is obtained, which has the following characteristics and properties.

PEN has a structure with a rigid double aromatic ring, whose presence in the polymeric chain accounts for many of the improvements which this polymer shows with respect to PET, such as, for example, a greater resistance, a higher thermal stability and improved barrier properties. PEN also has a higher glass transition temperature and a reduced gas permeability. This polymer has found extremely interesting applications in the field of films, fibres, packaging, above all for drinks and food, and is considered as being a product which can have extremely important applications.

The high cost, however, of 2,6-naphthalene-dicarboxylic acid is one of the problems (together with problems relating to disposal and mainly recycling) which has so far hindered a full development of this polymer.

The importance of finding alternative methods for inserting aromatic groups in the chains of polyester resins, unsaturated polyester resins, thermoplastic polyester resins and polyurethane resins, is therefore evident.

The identification of alternative methods which allow the insertion, together with aromatic groups or, alternatively, other functional groups such as imine groups or double bonds, into the chains of polyester resins, un-saturated polyester resins, thermoplastic polyester resins and polyurethane resins, is also of general interest.

The present invention therefore proposes to overcome the drawbacks present in the known technique.

It has been surprisingly found that the aromatic glycols and/or polyols according to the present invention allow various functional groups to be contemporaneously inserted into polyester chains or polymeric chains, in an extremely simple and economically convenient way, and with excellent yields.

In particular, an object of the present invention relates to a compound having the following general formula (A):

wherein:
R represents a residue obtained by substituting m hydrogen atoms by a compound selected from

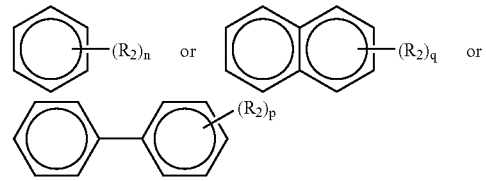

or a saturated aliphatic chain, linear or branched, having from 2 to 18 carbon atoms or an unsaturated aliphatic chain, linear or branched, having from 2 to 18 carbon atoms and with at least one double bond;

wherein $R_2$, the same or different when n, p or q are greater than or equal to 2, represents a linear or branched alkyl group, having from 1 to 18 carbon atoms;

n varies from 0 to 4;
p varies from 0 to 6;
q varies from 0 to 8;
$R_1$, the same or different, represents a hydrogen atom, an alkyl group optionally substituted, having from 1 to 6 carbon atoms or an aromatic group optionally substituted;
m is equal to 2, 3 or 4.

In particular, when R represents a phenyl radical and m is equal to 2, the substituents —(CONH—$CHR_1OH$)$_m$ can be in ortho, meta or para position, respectively, preferably in meta or para position.

When R represents a phenyl radical and m is equal to 3, the substituents —(CONH—$CHR_1OH$)$_m$ are preferably in position 1,3,5 or 1,2,4.

In particular, when R represents a phenyl radical and m is equal to 4, the substituents —(CONH—$CHR_1OH$)$_m$ are preferably in position 1,2,4,5.

Preferably, when R represents a naphthalene radical and m is equal to 2, the substituents —(CONH—$CHR_1OH$)$_m$ are respectively in position 2 and 6.

When R represents a biphenyl radical and m is equal to 2, the substituents —(CONH—$CHR_1OH$)$_m$ are in para position.

m is preferably equal to 2.
n, p and q are preferably equal to 0 or 1.

A further object of the present invention relates to the use of the compound having general formula (A) as monomer in polycondensation and polymerization reactions.

In particular, the compound according to the present invention can be used as monomer in polycondensation and/or polymerization reactions with suitable comonomers to produce saturated and unsaturated polyester resins with aromatic polyacids, polyamide resins, polyurethane resins or liquid crystal polymers.

A further object of the present invention relates to the polymer obtained by the polycondensation of terephthalic acid with the glycol of 1,4-benzenedicarboxyamide which has the following structure:

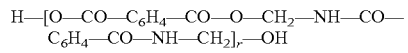

wherein r is greater than or equal to 4.

The main advantage of the compound according to the present invention is that it allows the contemporaneous insertion into polyester or polymeric chains of several functional groups, in an extremely simple and economically convenient way, with excellent yields. In particular, the contemporaneous insertion of aromatic rings and —CONH— groups, is particularly advantageous. The —CONH— groups enhance resistance to high temperatures and allow a reduction in the formation of by-products (for example acetaldehyde) of the polymers during the subsequent melting and extrusion.

The insertion of the double bond which allows the hardening of the thermosetting unsaturated polyester resins, is also particularly advantageous.

Another advantage of the polymers obtained by the polycondensation and/or polymerization of the aromatic glycols or polyols according to the present invention is that their properties are such as to allow them to be used for the production of containers, for example bottles, with an increased impermeability of the wall of the container both from the inside towards the outside of the container ($CO_2$), and also from the outside towards the inside of the container ($O_2$), thus allowing it to be used for an improved packaging of carbonated drinks and products sensitive to oxygen such as wines, beer, liquors, soft drinks, food substances.

The compound according to the present invention having general formula (A), is prepared by means of the following reaction:

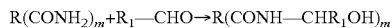

$$R(CONH_2)_m + R_1\text{—CHO} \rightarrow R(CONH\text{—}CHR_1OH)_m$$

wherein R, m and $R_1$ have the meanings previously indicated, and i.e. by reaction of the corresponding amide in a slightly basic solution with the aldehyde suitably substituted at a temperature ranging from 10° C. to 180° C., at a pressure ranging from 0 to 15 atm and for a time which varies from 5 minutes to 5 hours.

The reaction is preferably carried out in the presence of a basic anionic resin insoluble in the reaction medium, wherein the reaction medium is water. The temperature preferably varies from 60° C. to 120° C.

The pressure is preferably within the range of 2 to 5 atm, whereas the reaction is preferably carried out for a time varying within the range of 20 minutes to 1 hour.

$R(\text{—CONH}_2)_m$ is preferably selected from amides of terephthalic acid, isophthalic acid, 2,6-naphthalene-dicarboxylic acid, trimesic acid, pyromellitic acid or trimellitic acid.

$R_1CHO$ is preferably selected from formaldehyde and benzaldehyde.

A first application example of the compound according to the present invention is its use as monomer for the production of a thermosetting, unsaturated, orthophthalic polyester resin.

According to the state of the art, the thermosetting, orthophthalic unsaturated polyester resin is prepared by the reaction of phthalic anhydride with the first comonomer which is propylene glycol and with the second comonomer which is maleic anhydride to have the double bond which forms the bridge with styrene.

With the use of the compound according to the present invention, obtained from the amide of maleic anhydride and the aromatic glycol already containing the functional groups (double bond and aromatic ring), resins are obtained with much better physico-chemical characteristics.

The advantage is that the comonomer (in the case of the resin with phthalic anhydride) is a glycol which, in addition to the presence of the necessary functional groups, such as the phenyl ring and double bond, and consequently in addition to providing the end-product with the properties associated with the presence of said functional groups, has much lower costs than those of propylene glycol.

The characteristics and advantages of the composition according to the present invention can be better understood with the help of the following detailed and illustrative description.

EXAMPLE 1

A solution containing 1 mole of maleic diamide equal to 114.07 g in 500 g of methyl alcohol and a solution of 2.05 moles of formaldehyde in the form of a solution in water at 40%, are fed to a static mixer which also acts as heater and the liquid mixture of the two products indicated above is brought to a temperature of 70° C.

The mixture is then directly injected into a reactor containing an anionic resin, Amberliste XE275, the feeding rate of the mixture being regulated so that the residence time is not less than 1.5 minutes and not more than 5 minutes.

The mixture thus treated is fed to a fractionation column for the recovery of the methyl alcohol.

The aqueous mixture obtained at the bottom of the fractioning column is extracted with ethyl ether; after evaporation of the ethyl ether, glycol is obtained

$$HOCH_2\text{—CONH—CH}=\text{CH—CONH—}CH_2OH$$

with yields higher than 98%.

EXAMPLE 2

A solution containing 1 mole of adipic diamide equal to 144.18 g in 500 g of methyl alcohol and a solution of 2.05 moles of formaldehyde in the form of a solution in water at 40%, are fed to a static mixer which also acts as heater and the liquid mixture of the two products indicated above is brought to a temperature of 70° C.

The mixture is then directly injected into a reactor containing an anionic resin, Amberliste XE275, the feeding rate of the mixture being regulated so that the residence time is not less than 1.5 minutes and not more than 5 minutes.

The mixture thus treated is fed to a fractionation column for the recovery of the methyl alcohol.

The aqueous mixture obtained at the bottom of the fractioning column is extracted with ethyl ether; after evaporation of the ethyl ether, glycol is obtained

$$HOCH_2\text{—CONH—}(CH_2)_4\text{—CONH—}CH_2OH$$

with yields higher than 98%.

EXAMPLE 3

A solution containing 1 mole of isophthalic diamide equal to 164.13 g in 500 g of methyl alcohol and a solution of 2.05 moles of formaldehyde in the form of a solution in water at 40%, are fed to a static mixer which also acts as heater and the liquid mixture of the two products indicated above is brought to a temperature of 70° C.

The mixture is then directly injected into a reactor containing an anionic resin, Amberliste XE275, the feeding rate of the mixture being regulated so that the residence time is not less than 1.5 minutes and not more than 5 minutes.

The mixture thus treated is fed to a fractionation column for the recovery of the methyl alcohol.

The aqueous mixture obtained at the bottom of the fractioning column is extracted with ethyl ether; after evaporation of the ethyl ether, glycol is obtained

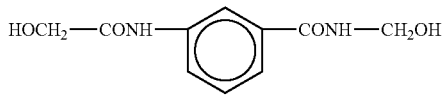

with yields higher than 98%.

I claim:

1. A compound having the following general fomula $R(CONH—CHR_1OH)_m$ wherein: R represents a naphthalene radical and m is 2; $R_1$ is the same or different, represents a hydrogen atom, an alkyl group optionally substituted, having from 1 to 6 carbon atoms or an aromatic group optionally substituted and the substituents —CONH—$CHR_1OH$ are in positions 2 and 6 on the naphthalene radical.

2. A compound having the following general formula $R(CONH—CHR_1OH)_m$ wherein: R represents a biphenyl radical where in is 2; $R_1$ is the same or different and represents a hydrogen atom, an alkyl group optionally substituted, having from 1 to 6 carbon atoms or an aromatic group optionally substituted; and the substituents —CONH—$CHR_1OH$ are in the para position on the biphenyl radical.

* * * * *